United States Patent [19]

Smith-Lewis

[11] Patent Number: 4,988,627
[45] Date of Patent: Jan. 29, 1991

[54] TEST DEVICE WITH DRIED REAGENT DROPS ON INCLINED WALL

[75] Inventor: Margaret J. Smith-Lewis, Pittsford, N.Y.

[73] Assignee: Eastman Kodak Company, Rochester, N.Y.

[21] Appl. No.: 136,164

[22] Filed: Dec. 18, 1987

[51] Int. Cl.$^5$ .................. G01N 21/03; G01N 33/545; G01N 33/76

[52] U.S. Cl. ..................................... 436/165; 436/166; 436/169; 436/178; 436/808; 436/510; 436/531; 436/532; 436/533; 422/56; 422/58; 422/61; 422/101; 422/102; 435/7.1; 435/299; 435/810; 435/7.5

[58] Field of Search ................................. 436/165–166, 436/169, 177, 178, 808, 814, 510, 532, 533, 65, 531; 422/56, 58, 61, 101, 102; 435/7, 299, 810

[56] References Cited

U.S. PATENT DOCUMENTS

| | | | |
|---|---|---|---|
| 3,741,876 | 6/1973 | Guilbault et al. | 195/103 R |
| 3,862,302 | 1/1975 | Price et al. | 436/814 X |
| 4,387,164 | 6/1983 | Hevey et al. | 422/56 X |
| 4,433,057 | 2/1984 | de Gracia | 436/65 |
| 4,496,654 | 1/1985 | Katz et al. | |
| 4,508,829 | 4/1985 | Sulitzeanu | 436/65 X |
| 4,639,419 | 1/1987 | Olson et al. | 436/814 X |
| 4,693,834 | 9/1987 | Hossom | 422/101 X |
| 4,738,823 | 4/1988 | Engelmann | 422/56 |
| 4,818,677 | 4/1989 | Hay-Kaufman et al. | 422/56 X |
| 4,833,087 | 5/1989 | Hinckley | 435/287 |
| 4,847,199 | 7/1989 | Snyder et al. | 422/101 X |
| 4,857,453 | 8/1989 | Ullman et al. | 422/58 X |

OTHER PUBLICATIONS

Richard L. Columbus, et al, "Architextured" Fluid Management of Biological Liquids, *Clin. Chem.*, vol. 33, p. 1531.

*Primary Examiner*—Robert J. Hill, Jr.
*Assistant Examiner*—Lynn M. Kummert
*Attorney, Agent, or Firm*—Dana M. Schmidt

[57] ABSTRACT

An immunoassay test device is disclosed with dried reagent drops applied to a sloping side wall of a reaction well. A method of applying them as liquid drops is also described, wherein the slope of the side wall, and the composition and volume of the liquid drop are selected to insure that the liquid drops do not flow down to the bottom of the well.

10 Claims, 2 Drawing Sheets

TEST DEVICE WITH DRIED REAGENT DROPS ON INCLINED WALL

FIELD OF THE INVENTION

This invention relates to an immunoassay test device and a method of applying reagents to the device for optimum performance of the assay.

BACKGROUND OF THE INVENTION

Immunoassays are either currently in use, or planned for use, in detecting infectious disease such as Streptococcus, sexually transmitted diseases such as herpes viruses or chlamydia, and/or pregnancy via the detection of hCG (human chorionic gonadotropin). Drugs are also detectable. Appropriate devices have been developed to run such assays either at a doctor's office or the patient's home, using samples taken from the patient, such as urine. For example, useful devices are described in commonly owned U.S. Ser. No. 98,248 filed by Charles C. Hinckley et al on Sept. 18, 1987, entitled "Sliding Valve For Vent of Liquid Collecting Compartment." The details of that application are expressly incorporated herein by reference.

As described in the aforesaid application, such devices can include one or more chambers containing some of the reagents, each chamber having a sloping side wall that forms a well. At the bottom of each well is a membrane that is porous enough to pass liquid through, but constructed to retain an immunoproduct produced when the analyte in question is present in the patient's sample. The immunoreagents are described in that application as being coated onto the chamber side wall or added by the user. No details are given as to how a coating is to be applied, nor is it stated therein whether the coating is to be a uniform coating or in discrete locations only.

In some assays, such as the pregnancy assay for hCG, the reagents that are pre-incorporated in the chamber include biotinylated antibody for the antigen that is the analyte, and a buffer. The buffer is needed because patient's sample, for example, urine, comes in such a wide range of pH, and the assay works optimally at a pH about 6 to 8. For ease in manufacturing, such buffer is preferably deposited as an essentially fully saturated solution at about 50 wt % concentration, in about 8 $\mu$l, to permit the use of small sized drops.

In the hCG assay, at least some of the biotinylated antibody and the buffer need to be deposited on the side wall of the chamber well, rather than on the membrane, because the reaction between biotin and avidin should not take place before patient's sample is added, and certainly not when the device is manufactured. Otherwise the biotinylated antibody is not free to migrate through a solution standing above the membrane to complex with available antigen.

Therefore, at least some of the biotinylated antibody must be deposited and kept on the sloping side wall, until dried.

In addition, some of the buffer is not deposited onto the membrane because (1) the pores of the membrane are too few to retain all the buffer, and (2) even if it could be so retained during manufacturing, much of the buffer so located will wash through too early in the incubation stage during use, if it is initially located in the membrane. That is, a patient sample is designed to "stand" above the membrane for incubation. However, the initial wetting of the membrane by the patient sample causes immediate inadvertent wash through of any reagent in, but not bound to, the membrane. In that case, the buffer would not be retained in the well above the membrane where it is needed to maintain the pH of the patient sample for the antibody complexing reaction.

Nevertheless, prior to this invention it has not been readily apparent how to merely deposit or place liquid containing reagents, onto the sloping side wall without that liquid pouring down onto the membrane instead of drying in place. Cementation of liquid drops to the side wall, followed by drying, is of course inappropriate, in that the reagent must be capable of re-dissolving when patient liquid is added. The problem is particularly aggravated by the fact that the preferred material for the wall construction—a dyed polystyrene—has a lower tolerance for drop adherence than other wall materials, for example polystyrene not containing a dye preincorporated into it.

It would be conceivable to construct the well with a horizontal shelf in the wall that provides a level platform for location of the drops. One difficulty with such an arrangement is that it becomes very difficult to force all the liquid off such a shelf, and down onto the membrane where separation of bound and free labeled antibody occurs.

Alternatively, the slope of the wall could be rendered more gradual, to the point at which almost any volume drop will stick to any surface. This is not viable either, as a slight decrease in the wall slope drastically increases the amount of sample volume that has to be used for a given exposed area of membrane. In addition, the area of the membrane can not be reduced much, since it then becomes difficult to detect a color change on the membrane.

Thus, for the reasons given above, the sloping wall is generally restricted to an angle of at least 60°, for example about 65°, and the exposed membrane surface area is about 0.2 cm$^2$.

SUMMARY OF THE INVENTION

I have determined that the immunoreagent and/or buffer can be applied as drops on the sloping side wall of the well of the device, without the drops flowing down the wall, under certain specific conditions.

More specifically, in accord with one aspect of the invention, there is provided a test device for conducting an immunoassay, the device comprising (a) a chamber well containing a reagent selected from at least one immunoreagent and a buffer, the well having at least one wall sloped at a predetermined non-zero angle to the horizontal when in use, and (b) a membrane at the bottom of the well, the membrane being porous to liquid and relatively non porous to a complex comprising said immunoreagent and an analyte to which the immunoreagent is specific. The device is improved in that at least some of the buffer or the immunoreagent is in at least one dried, water redissolvable deposit on the sloping wall above said membrane, formed from an aqueous drop placed on the wall above the membrane, and wherein the angle of the sloping wall, and the volume and the composition of the aqueous drop containing said buffer or immunoreagent, are selected to prevent the placed drop from flowing down to the membrane.

In accord with another aspect of the invention, there is provided a method for manufacturing a test device for an immunoassay using a reagent selected from at least one immunoreagent and a buffer, comprising the steps of (a) providing a chamber well having at least one wall sloped at a predetermined, non-zero angle to the horizontal when in use and, at the bottom of the well, a membrane that is porous to liquid and relatively non-porous to a complex comprising the immunoreagent and an analyte to which the immunoreagent is specific;

(b) depositing on the sloped wall above the membrane, at least one aqueous drop, the drop having a predetermined volume and a composition that includes at least some of said buffer or said immunoreagent, said composition being selected such that for the volume of the drop and the predetermined angle of the sloped wall, the deposited drop does not flow down to the membrane;

and (c) drying the drop.

Thus, it is an advantageous feature of the invention that a device can be prepared which retains some of the reagents, defined herein to include both the immunoreagent and the buffer, on the sloping side wall of the well rather than on the membrane.

It is a related advantageous feature of the invention that the reagents of such a device are located in position to react efficiently with the patient sample deposited above the membrane at the bottom of the well, rather than prematurely wash through the membrane or react with the membrane.

Yet another advantageous feature of the invention is that the reagents are located so as to not prematurely contact each other.

Other advantageous features will become apparent upon reference to the following Description of the Preferred Embodiments, when read in light of the attached drawings.

DESCRIPTION OF THE PREFERRED EMBODIMENTS

The invention is described hereinafter for a preferred test device wherein all of the buffer and the antibody of the assay are located on a sloped polystyrene wall of the well, each in separate drops, used to assay for hCG. In addition, the invention is useful when only some of each of the antibody or buffer is on the wall, the remainder being on the membrane. Indeed, the invention is applicable to only some of the buffer being on the side wall, with all of the immunoreagent being on the matrix, as explained hereafter. It is also useful if some of the buffer is included in the drops of antibody, subject to the restrictions noted hereinafter. Still further, it is useful regardless of the material used for the wall of the well, the particular material selected being of course critical in dictating just how large a slope angle can be tolerated before the drop rolls off the wall instead of staying in place (at the given volumes provided for the drop). Still further, the invention is useful regardless of which analyte is being assayed —that is, it is useful for others besides hCG. Thus, it is useful with assays requiring only an immunoreagent and no buffer.

As used herein "immunoreagent" includes any receptor specific for a particular ligand, usually an analyte of a patient sample. Representative ligands detectable with the present invention include primary amines, amino acids, peptides, polypeptides, proteins, lipoproteins, glycoproteins, drugs, haptens, enzymes, steroids, lipids, nucleic acids, hormones, vitamins, polysaccharides, glycolipids, alkaloids, organisms (bacteria, protozoa, fungi, viruses including retroviruses, rickettsia and the like) and components thereof, blood components, tissue and organ antigens and other materials known to one skilled in the art. In some instances, the ligand is an antibody which is directed against a drug, hormone, antibiotic or other compound having antigenic properties. Alternatively, the ligand can be an antigenic material, an antibody which is directed against another antibody (that is, an anti anti-body). Both monoclonal and polyclonal antibodies can be used, and they can be whole molecules or various fragments thereof. Preferably, monoclonal antibodies are used in the assays.

In a preferred embodiment, the test device is useful for the detection of hCG as an early indicator of pregnancy, where the immunoreagent is a biotinylated antibody to hCG.

Figure 1:
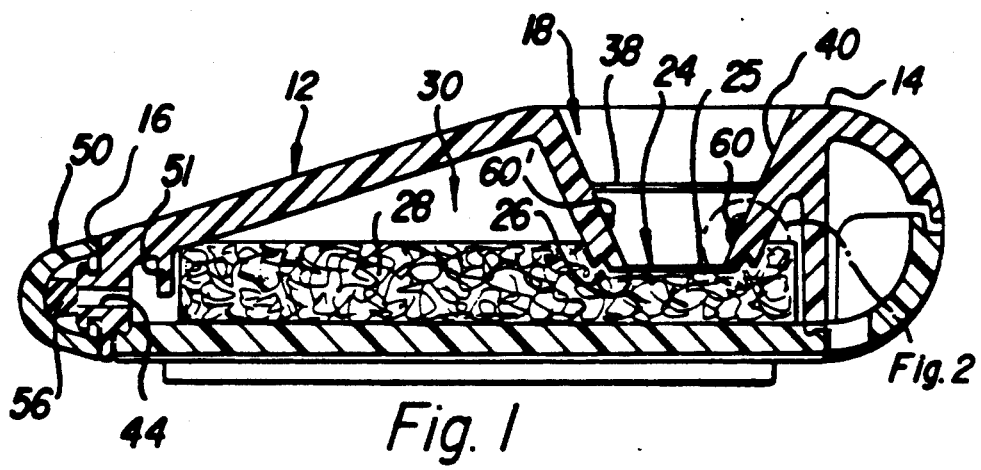
FIG. 1 is a section view in elevation through a device constructed in accord with the invention.

A device 10 with which the invention is useful comprises, FIG. 1, a frame 12 having a top surface 14, and a front edge 16. Mounted on edge 16 is a slide valve 50. Top surface 14 has at least one and preferably three wells or upper compartments 18 formed by a sloping side wall 40. At the bottom of each of the compartments is a filter 24 of appropriate pore size and pore volume. Filter 24 has an upper surface 25 and an under surface 26, FIG. 2. Surface 26 is in liquid-flow contact with an absorbent material 28 that preferably occupies each of the lower compartments 30, FIG. 1, paired with the upper ones. As used herein, "liquid flow contact" means, in sufficient proximity such that a liquid meniscus emanating from surface 26 will also wet material 28 and flow into it, if no air lock exists in the lower compartment. Material 28 is any bibulous material, having a sufficient pore volume to soak up about 2 cc of liquid. Useful materials include cellulose acetate, cotton, and rayon. Useful materials for filters 24 include polyamides, such as nylons, and for example nylon-66 microporous membranes manufactured under the tradenames BIODYNE A or ULTIPOR N-66 or LOPRODYNE by Pall Corporation. The membranes may be precoated or pretreated (prior to use) with one or more water soluble proteins, such as casein derivatives obtained from acylation, alkylation or sulfonylation of the casein.

In any event material 24 is selected to be porous to the liquid but relatively non porous to the immunoproduct of choice. As used herein, "relatively non-porous" means sufficiently non-porous as to trap for detection the immunoproduct, or the product of the reaction between the immunoreagent and the analyte of the patient's sample. For example, a sandwich assay can be used, with an immunoreagent for the antigen of choice being bound to beads. That immunoreagent can be disposed solely on the matrix, given a material 24 with pore sizes that are too small to allow the beads to pass through. The other immunoreagent of the sandwich assay that bears the detectable tag or label, is added by the patient during the test, and is not initially in the compartment. Thus, only the buffer need be on the side wall in such case, pursuant to the invention as detailed hereinafter. (The tagged immunoreagent is able to pass through material 24, unless it forms a sandwich immunoproduct.)

Optionally the device can contain (between the filter and the absorbent material) a porous member which restricts flow back up to the membrane, but allows flow from the membrane to the absorbent material.

Optionally, a liquid level indicator ridge 38, FIG. 1, is provided in the wall 40 of each well, as a circular ring. Alternatively, such an indicator can be one or two rings or fragments of a ring vertically spaced on wall 40, or a vertical bar or dot (not shown).

Vent aperture 44 is provided in each compartment 30 to allow air passage out of the compartment as liquid flows in. Without such vents, or when the vent apertures are closed, an air lock precludes most of the liquid from flowing through filter 24 into the lower compartments. Slide valve 50 includes an elastomeric material 56 selected to insure that the value can be slid off vent 44 or onto it with a force between about 0.15 newtons and about 10 newtons, when material 56 is compressed about 0.15 mm.

In accordance with the invention, at least some of the reagents are located on side wall 40 as one or more dried drops 60, 60' FIG. 1. Most preferably, all of the immunoreagent and all of the buffer are so located, in at least one drop 60 for the buffer, and at least one drop 60', FIG. 3, for the immunoreagent and its attendant addenda. Because of the preferred amount (3 $\mu$g in 8 $\mu$l of immunoreagent and 4 mg in 8 $\mu$l of buffer), about four drops of 2 $\mu$l each of buffer are preferred and about 4 drops of 1 $\mu$l each of immunoreagent are preferred. Both sets of drops are preferably smaller than 4 $\mu$l, because for one reason such smaller volumes dry faster. It is further preferred that the drops be plural in number, to facilitate a more rapid redissolving than would be the case if all the buffer or all the immunoreagent were in just one drop.

Preferably the immunoreagent is a biotinylated anti-hCG antibody that will react with avidin attached to polymeric beads that are retained on the membrane. Alternatively, the immunoreagent on wall 40 can be a labeled antibody that permits the retained complex to be detectable.

Any buffer is useful, provided it maintains the desired pH range. For the preferred hCG assay, the preferred pH range is from about 6 to 8, as noted above. For this, the preferred buffer is the MOPS buffer, which is 3-(N-morphilino)propanesulfonic acid, available from commercial sources.

Optionally an acrylamide polymer is also included as an addendum, particularly in the drops containing the immunoreagent. As described in my commonly owned U.S. application Ser. No. 136,211 filed on 12-18-87, entitled "Use of Immobilized Biotinylated Receptor in Test Device, Kit and Method for Determining a Ligand", such polymers are useful in improving the keeping of the immunoreagent during manufacture and storage of the device, particularly for immunoassays of hCG. Useful acrylamide polymers include, but are not limited to, acrylamide homo-and copolymers. Useful copolymers are prepared from two or more ethylenically unsaturated polymerizable monomers, at least 50 weight percent of the combined monomer weight being acrylamide. Preferred polymers include, but are not limited to, poly(acrylamide), poly(acrylamide-co-1-vinyl-2-pyrrolidone)(90:10 weight ratio), poly(acrylamide-co-1-vinyl-2-pyrrolidone)(50:50 weight ratio), poly(acrylamide-co-1-vinylimidazole) (90:10 weight ratio), poly(acrylamide-co-2-methyl-1-vinylimidazole)(90:10 weight ratio), poly(acrylamide-co-N-methylolacrylamide)(80:20 weight ratio), poly(acrylamide-co-acrylic acid)(90:10 weight ratio), poly(acrylamide-co-2-vinylpyridine)(89:11 weight ratio), poly(acrylamide-co-2-methyl-5-vinylpyridine)(90:10 weight ratio), and poly(acrylamide-co-1-vinyl-2-pyrrolidone-co-acrylic acid) (75:15:10 weight ratio). More than one acrylamide polymers can be used if desired, and different ones can be used for different immunoreagents or in different wells.

The acrylamide polymer may or may not be included with the buffer drops as addenda. It has been found that its presence is helpful in retaining the drops of buffer in place on the walls when the device experiences severe vibration during manufacturing, for example, when manufacturing using automated equipment. However, if manufacture is done by hand, the acrylamide polymer can be omitted entirely from the buffer drops.

Figure 2:
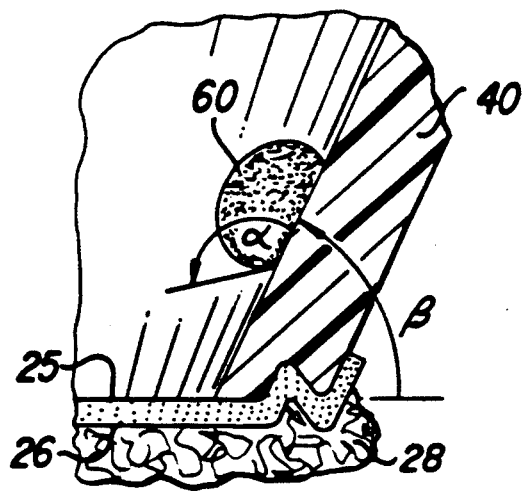
FIG. 2 is a fragmentary, enlarged section view illustrating the well marked FIG. 2 in FIG. 1 in greater detail in its manufacturing stage.
Figure 3:
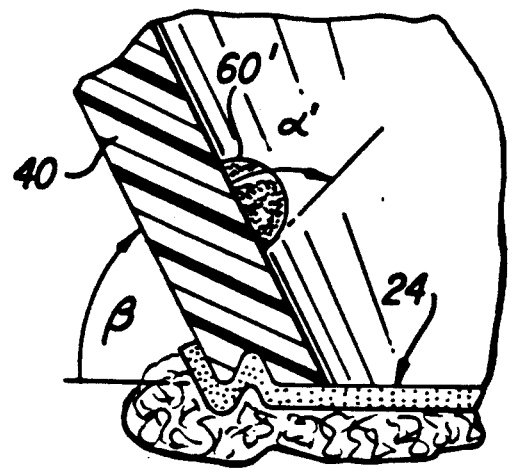
FIG. 3 is a section view similar to that of FIG. 2, but of the immunoreagent drop portion of the well.

The critical aspects in locating the dried drops on wall 40 as shown are aspects defined by the drop in its liquid state, and the wall, FIGS. 2 and 3. These are, the drop volume, the drop composition, and properties of wall 40 as they relate to that drop. That is, depending upon the material and surface condition of wall 40, there is a particular angle of the sloping wall at which the drop will experience incipient flowing, and thus, "failure" as far as this invention is concerned. As described in R. L. Columbus et al, "Architextured Fluid Management of Biological Liquids", 33 Clin. Chem. 1531 (1987), the values of the advancing contact angle and the receding contact angle of the drop at the point of incipient flow are values that define the "contact angle hysteresis".

However, measurements of such advancing and receding contact angles at the point of incipient flow are extremely difficult. More controlling, and measurable, as reported hereinafter, is the wall angle beta at such point of incipient flow, and the volume of the drop. Even "wettability", as measured by the static contact angle gamma the drop forms on the same wall surface at a zero angle of slope—that is, while horizontal, FIG. 4—does not appear to be a significant factor for this invention.

The above described values have been determined for the buffer drops and immunoreagent drops of choice, by using a simplified test. This test is applied to a preferred side wall surface at various values of angle beta. For these experiments, the wall surface was exactly the same material as is preferred for side wall 40, that is, relatively smooth (as defined hereinafter) polystyrene having a grey dye preincorporated into the polymer prior to molding the surface. As used herein, "relatively smooth" refers to an SPE-SPI number 3 surface, as measured by the SPE-SPI standard published by the Society of the plastic Industry. It has been found that randomly roughened versions of such a surface are less likely to hold the desired drops in place, as is predicted by the aforesaid article by R. L. Columbus et al.

EXAMPLES 1-10

Figure 4:
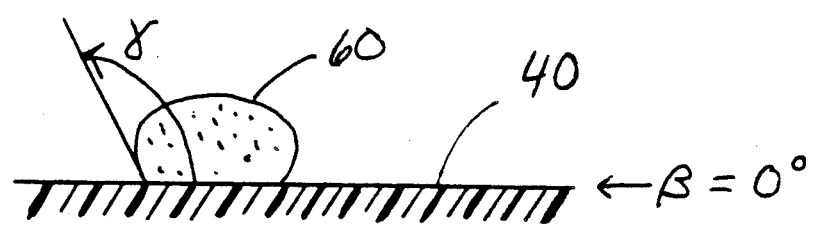
FIG. 4 is an elevational view in section illustrating the measurement of the static contact angle.

More specifically, the following liquids were tested, both to determine the angle beta at which incipient failure (flow) occurs, and the static contact angle gamma, FIG. 4, for that liquid on the same polystyrene surface. All drops were adjusted to be at a pH of 7.5.

(This test is applicable to any candidate liquid.) In the table, "viscos" means "viscosity", measured in centipoise at room temperature.

TABLE I

Liquids Tested

| Ex | COMPOSITION | CONCENTRATION | DROP VOL. ($\mu$l) | VISCOS (CPS) | SURFACE TENSION (dynes-/cm)* |
|---|---|---|---|---|---|
| 1 | Mops Buffer | 2.5 moles/l | 4 | 5.80 | 65.9 |
| 2 | Mops Buffer | 2.5 moles/l | 10 | 5.80 | 65.9 |
| 3 | Ex. 1 Plus poly(acrylamide) | 3.75 mg/ml for the addendum | 4 | 6.72 | 66.2 |
| 4 | Ex. 1 plus poly(acrylamide) | 3.75 mg/ml for the addendum | 10 | 6.72 | 66.2 |
| 5 | Ex. 1 plus Zonyl FSN surfactant, a nonionic fluorochemical surfactant manufactured by DuPont Company | 0.01% (w/v) of the surfactant addendum | 4 | 6.26 | 24.1 |
| 6 | Ex. 1 plus Zonyl FSN surfactant, a nonionic fluorochemical surfactant manufactured by DuPont Company | 0.01% (w/v) of the surfactant addendum | 10 | 6.26 | 24.1 |
| 7 | Ex. 3 plus Zonyl FSN surfactant, a nonionic fluorochemical surfactant manufactured by DuPont Company | 0.01% (w/v) of the surfactant addendum | 4 | 6.91 | 24.4 |
| 8 | Ex. 3 Plus Zonyl FSN surfactant, a nonionic fluorochemical surfactant manufactured by DuPont Company | 0.01% (w/v) of the surfactant addendum | 10 | 6.91 | 24.4 |
| | biotinylated anti-hCG antibody plus poly(acrylamide) plus "Uvitex OB", a fluorescing agent for quality control manufactured by Ciba Geigy | 0.375 mg/ml  7.5 mg/ml  5 mg/ml | 4 | 1.40 | 59.2 |
| 10 | biotinylated anti-hCG antibody plus poly(acrylamide) Plus "Uvitex OB", a fluorescing agent for quality control manufactured by Ciba-Geigy | 0.375 mg/ml  7.5 mg/ml  5 mg/ml | 10 | 1.40 | 59.2 |
| Comparative Ex. A | Ex. 9 plus Zonyl FSN surfactant | 0.01% (w/v) of the FSN addendum | 4 | 1.29 | 24.7 |
| Comparative | Ex. 9 plus Zonyl FSN | 0.01% (w/v) of the FSN | 10 | 1.29 | 24.7 |

TABLE I-continued

| Ex | COMPOSITION | Liquids Tested CONCEN- TRATION | DROP VOL. (μl) | VISCOS (CPS) | SURFACE TENSION (dynes- /cm)* |
|---|---|---|---|---|---|
| Ex. B | surfactant | addendum | | | |
| Control 1 | distilled water | — | 4 | 1.0 | 72.4 |
| Control 2 | distilled water | — | 10 | 1.0 | 72.4 |

*Measured at room temperature.

The above comparative examples were added only to illustrate the effect of surfactant on the drops' static contact angle. For the purpose of the invention, no surfactant is needed.

The experiment was done as follows:

The sample liquid for each of the above examples was dispensed in the indicated volume onto a flat surface of two different materials. Material #1 was the material of wall surface 40 having an SPE-SPI surface smoothness of 3, while material #2 was undyed polystyrene of generally the same surface smoothness. In both cases the material was kept horizontal, FIG. 4, so that a static contact angle gamma could be measured. The surface was then incrementally tilted 5° at a time, to ascertain when incipient failure (that is, flow downwards) initiated. The results appear in Table 11.

TABLE II

| | | Results | | | |
|---|---|---|---|---|---|
| | | MATERIAL #1 | | MATERIAL #2 | |
| Ex. | Drop Vol. | Static Contact Angle | Angle of Incipient Failure | Static Contact Angle | Angle of Incipient Failure |
| 1 | 4 | 86° | D.N.F.* | 78° | D.N.F. |
| 2 | 10 | 85° | 10° | 79° | 60° |
| 3 | 4 | 85° | D.N.F. | 79° | D.N.F. |
| 4 | 10 | 87° | 15° | 85° | 70° |
| 5 | 4 | 84° | D.N.F. | 75° | 90° |
| 6 | 10 | 86° | 15° | 80° | 90° |
| 7 | 4 | 81° | D.N.F. | 75° | D.N.F. |
| 8 | 10 | 82° | 15° | 79° | 90° |
| 9 | 4 | 91° | D.N.F. | 83° | D.N.F. |
| 10 | 10 | 92° | D.N.F. | 84° | D.N.F. |
| Comparative Ex. A | 4 | 65° | D.N.F. | 65° | D.N.F. |
| Comparative Ex. B | 10 | 67° | D.N.F. | 73° | 90° |
| Control 1 | 4 | 91° | D.N.F. | 89° | D.N.F. |
| Control 2 | 10 | 91° | 25° | 90° | 70° |

*D.N.F. = Did not flow, even at 90°.

These results indicate that for material No. 1, the plastic material of choice for the device, the drop volume for the buffer had to be less than 10 μl, since the angle of incipient failure for such a volume was in most cases less than 60° (the needed angle of beta as noted above). The antibody drops can be that large, but practicalities dictate a smaller size since not that much antibody is needed and drying is facilitated. On the other hand, for volumes of 4 μl (or less), the incipient failure never occurred (as indicated by "greater than 90°"). For these reasons, the preferred volume is 4 μl or less and preferably about 2 μl. From these tests, it is not clear at what larger volume the failure angle approaches 60°. As to the static contact angle and viscosity, no clear correlation was found, except that the preferred liquids and preferred polystyrene wall material in no case produced a static contact angle gamma less than 80°. As to surface tension, no correlation was seen in this test. However, some manufacturing techniques may create vibrations prior to drying. In such cases, factors other than the drop volume, composition of the liquid, and angle of the sloping wall, for example, surface tension, may affect the performance of the device.

EXAMPLES 11-12: 6 μl SIZED DROPS

To further explore the size of drops that might adhere at a beta angle of 60°, examples 1 and 3 were repeated, except at a volume of 6 μl and with beta adjusted at 5° increments from zero to 60°. In both cases, the drop did not fail to adhere, that is it remained adhering at 60°, the minimum desired angle for beta. Thus, a 6 μl drop is useful, but not preferred, in that this test did not take into account the possibility of subsequent vibrations incurred by wall 40 prior to drying. As was shown by the 10 μl examples, the larger volumes tend to fail at beta values less than 60°, so that drop volumes close to 10 μl are likely to fail after initially sticking without failure, if they are subjected to shaking or vibrations such as can occur in manufacturing.

In some instances, a single well can have more than one immunoreagent on the wall 40 as long as they are such that they do not interfere with each other, or are placed on the wall in such a manner that they do not interfere with each other. Each immunoreagent is deposited in a manner such that it is stable and inert to reaction until a liquid sample is added to redissolve it.

As noted above, the immunoreagent can also have some buffer with it in at least one drop, provided that the amount of buffer is such that it will not destroy the activity of the immunoreagent over a suitable keeping period, such as at least five months. For the hCG assay, this amount is preferably about 0.025 moles of buffer per liter of anti-hCG antibody drop solution.

A number of methods are usable in placing or depositing the drops onto the side wall. The liquid can be formed as a drop pendant from a pipette, and then moved preferably horizontally to the sidewall to touch it off as a complete drop onto the wall. Such a method can be done manually, or completely automatically. Alternatively, the liquid drops can be formed by an ink jet application, in which case each drop is preferably built up on the side wall by having suitable fractions of the drop ejected in closely spaced spurts. That is, in the case of the buffer drops, it is preferably applied in spurts of 0.1 to 0.15 mg lasting about 0.5 msec, every 50 to 200 msec. More broadly, the buffer liquid can be applied in similar amounts in spurts lasting from 0.3 msec to 0.7 msec, as frequently as 1 msec or as infrequently as 255 msec.

The antibody drops are applied by ink jet ejection in similar amounts, except of course the total volume of a completed drop is less.

Following deposition of the drops by either method, they are dried, leaving a deposit on the wall as shown in FIG. 1.

The device so constructed using 6 μl drops or less, was found to provide adequate redissolving using patient's sample, within the time period of the desired incubation.

The invention has been described in detail with particular reference to preferred embodiments thereof, but it will be understood that variations and modifications can be effected within the spirit and scope of the invention.

What is claimed is:

1. A method for manufacturing a test device for an immunoassay using a reagent selected from at least one immunoreagent and a buffer, comprising the steps of
    (a) providing a chamber well having at least one wall sloped at an angle of at least about 60° to the horizontal when in use, and at the bottom of said well, a membrane that is porous to liquid and relatively non-porous to a complex comprising said immunoreagent and an analyte to which said immunoreagent is specific, said wall comprising a material that makes a static contact angle with aqueous drops containing said buffer or immunoreagent, that is not smaller than about 80°,
    (b) depositing on said sloped wall above the membrane, at least one aqueous drop containing at least some of said buffer or said immunoreagent, in a volume that is no larger than about 6 μl so that said drop stays on the sloped wall and does not flow onto the membrane;
    and (c) drying said drop on the sloped wall.

2. A method as defined in claim 1, wherein said wall material comprises polystyrene having a surface smoothness of 3 measured as an SPE-SPI surface.

3. A method as defined in claim 1 wherein said drop composition further includes an acrylamide polymer at a concentration of about 0.375 weight percentage.

4. A method as defined in claim 1, wherein said drop contains buffer and no immunoreagent and further including the step, prior to said drying step (c), of
    (b') depositing on said sloped wall above said membrane, at least one other aqueous drop having properties generally identical to said drop of buffer, except that it includes some of said immunoreagent and is of a volume less than that of said drop of buffer.

5. In an article of manufacture for conducting an immunoassay, said article comprising (a) a chamber well containing a reagent selected from at least one immunoreagent and a buffer, said well having at least one wall sloped at a predetermined angle of at least about 60° to the horizontal when in use, and (b) a membrane at the bottom of said well, said membrane being porous to liquid and relatively non-porous to a complex comprising said immunoreagent and an analyte to which said immunoreagent is specific;

the improvement wherein at least some of said buffer or immunoreagent is in at least one dried, water-redissolvable deposit located on said sloping wall above said membrane, present in an amount no greater than that which can be deposited in an aqueous drop no larger than about 6 μl, and wherein said wall comprises a material that makes a static contact angle with aqueous drops containing said buffer or immunoreagent, that is not smaller than about 80°.

6. An article as defined in claim 5, wherein said material comprises polystyrene having a surface smoothness of 3 measured as an SPE-SPI surface.

7. An article as defined in claim 5, and further including in said deposit, an acrylamide polymer at a concentration of about 30 μg per 8 μl (0.375 weight percentage).

8. An article as defined in claim 5, wherein said drop contains buffer and no immunoreagent and wherein some of said immunoreagent is confined to at least one other dried, water-redissolvable deposit on said sloping wall above said membrane, said immunoreagent deposit being smaller in volume than said buffer deposit such that when placed as a drop on said wall for said angle of said sloping wall, the immunoreagent drop does not flow onto said membrane.

9. An article as defined in claim 8, wherein said immunoreagent is a biotinylated anti-hCG antibody.

10. An article as defined in claim 5, wherein said buffer is effective to maintain a pH of from about 6 to about 8.

* * * * *

UNITED STATES PATENT AND TRADEMARK OFFICE
CERTIFICATE OF CORRECTION

PATENT NO. : 4,988,627
DATED : January 29, 1991
INVENTOR(S) : Margaret J. Smith-Lewis It is certified that error appears in the above-identified patent and that said Letters Patent is hereby corrected as shown below:

Abstract, line 3 should read: --well. A method of applying them as liquid drops is also--.

Column 3, line 56 should read: --of the antibody or buffer is on the wall, the remainder--.

Column 7, line 56 should read: --9   biotinylated    0.375 mg/ml
4        1.40       59.2--.

Signed and Sealed this

Twenty-ninth Day of September, 1992

*Attest:*

DOUGLAS B. COMER

*Attesting Officer*     *Acting Commissioner of Patents and Trademarks*